United States Patent [19]

Scales-Medeiros

[11] Patent Number: 5,626,839
[45] Date of Patent: May 6, 1997

[54] LIGHT RESPONSIVE SELF-TANNING PRODUCTS AND METHODS FOR USE

[76] Inventor: Virginia Scales-Medeiros, 520 Eureka Ave., Santa Rosa, Calif. 95403

[21] Appl. No.: 337,489

[22] Filed: Nov. 8, 1994

[51] Int. Cl.$^6$ .............................. A61K 7/42; A61K 7/00
[52] U.S. Cl. .............................. 424/59; 424/401
[58] Field of Search .............................. 424/59, 401, 63; 606/2, 3, 9; 607/54

[56] References Cited

U.S. PATENT DOCUMENTS

| | | | |
|---|---|---|---|
| 2,104,492 | 3/1938 | Merkel . | |
| 2,949,403 | 8/1960 | Andreadis et al. | 167/90 |
| 3,988,437 | 10/1976 | Bradner | 424/59 |
| 4,434,154 | 2/1984 | McShane | 424/60 |
| 4,590,061 | 5/1986 | Southand et al. | 424/7.1 |
| 4,818,491 | 4/1989 | Fariss | 422/56 |
| 4,829,092 | 5/1989 | Nelson et al. | 514/738 |
| 4,913,897 | 4/1990 | Chvapil et al. | 424/59 |
| 5,061,480 | 10/1991 | Marchese | 424/59 |
| 5,196,705 | 3/1993 | Ryan | 250/372 |
| 5,302,378 | 4/1994 | Crotty et al. | 424/59 |
| 5,318,774 | 6/1994 | Alban et al. | 424/59 |
| 5,377,676 | 1/1995 | Vari et al. | 128/634 |

FOREIGN PATENT DOCUMENTS 1627938  2/1991  U.S.S.R. .

*Primary Examiner*—Sallie M. Gardner
*Attorney, Agent, or Firm*—Richard C. Litman

[57] ABSTRACT

Compositions, methods, and kits for cosmetically producing a tanned appearance in desired areas of skin. The composition includes a self-tanning agent together with intimately admixed fluorescent materials in a cosmetic carrier. Without prolonged exposure to intense solar or artificial radiation, applying the self-tanning agent imparts a tanned appearance which develops several hours to a day after application. The fluorescent materials absorb at one frequency, and emit at another visible frequency. The admixture of self-tanning agent and fluorescent materials allows application of the self-tanning agent selectively to desired areas of the skin. A light source which emits at the absorbing frequency of the fluorescent materials may be provided together with the compositions in kit form. By illuminating the skin after the composition has been applied and before the self-tanning agent develops its color, any coverage of undesired areas may be easily removed, and any desired areas which were unintentionally untreated may be detected and subject to reapplication.

11 Claims, No Drawings

LIGHT RESPONSIVE SELF-TANNING PRODUCTS AND METHODS FOR USE

BACKGROUND OF THE INVENTION

1. Field of the Invention

The present invention relates to self-tanning cosmetic products and methods. More particularly, a light-responsive fluorescent agent and a self tanning agent are combined in a cosmetic composition which may be detected with a matched light source, thereby indicating the presence and extent of composition coverage.

2. Description of the Prior Art

Naturally tanned skin is generally accepted to be the product of the physiological development and distribution of melanin, a skin pigment. When skin is exposed to radiant energy, especially light in the UV region, melanin is delivered to the skin surface. There it accumulates and oxidizes, giving the skin a darkened patina. This process is believed to afford a degree of natural protection for the skin against harmful UV overexposure.

Tanned skin is accordingly associated with outdoor activity, and is aesthetically desirable for many people. Unfortunately, it is not always possible to spend the requisite time under radiant exposure to develop a naturally tanned appearance. Further, exposure to UV radiation in sufficient quantity to develop a tan has many associated health risks. These include erythema, actinic skin damage, premature skin aging, and development of skin melanomas. Additionally, many people have skin complexions which do not tan readily. For example, the skin of some people with fair complexion reacts to UV radiation by developing small patches of color, or freckles, rather than a continuous tan.

For these reasons, cosmetic self-tanning agents have been developed in the prior art, and have achieved wide commercial acceptance. Self-tanning agents produce a color change in the skin without sun or other intense radiation exposure. U.S. Pat. Nos. 2,949,403 issued Aug. 16, 1960 to John T. Andreadis et al.; 5,318,774 issued Apr. 12, 1994 to Brian A. Crotty et al.; and 5,302,378 issued Jun. 7, 1994 to Noelle C. Alban et al. disclose various self tanning agents, formulations, and methods of use. Their disclosures are incorporated herein by reference. In conventional self tanning products, color change is not immediately developed, but gradually darkens the skin over a period of time from a few hours to a day or so, depending on the self-tanning agent and its formulation.

Upon developing, the color becomes fixed on and in the upper layers of skin, and like natural tans, may not be removed by normal bathing. The developed color slowly fades over several days to weeks, again simulative of natural tans. Unfortunately, if the self-tanning agent is applied to undesired areas of the skin, or if areas of the skin are not uniformly covered, the aesthetic quality of the resultant tan will be marred by imperfections. These imperfections will only show when color has developed in the skin and become very difficult or impossible to correct, due to the desired resistance to removal of these products, as noted above. Besides exercising care in applying self tanning formulations, the prior art is silent as to this problem.

Cosmetic formulations which include fluorescent pigments or dyes are known. These are typically used in face or body paints, lipsticks, and makeup wherein the fluorescent material produces brilliance, whitening, or color for a desired aesthetic appearance. Fluorescent compounds dispersed in sun-screening products have also been the subject of earlier patents. U.S. Pat. No. 3,988,437 issued Oct. 26, 1976 to Hugh Bradner, describes a sun-screening product in which fluorescent material is dispersed to absorb the harmful radiation of the sun and convert it into less harmful rays to tan the human skin. These compositions are formulated with inert carriers. No description is made in this patent of combining fluorescent materials with other active ingredients, nor using the fluorescent materials as indicators, since these materials fluoresce outside the visible spectrum.

Further, lamps which produce photo-luminescence in exposed surfaces are known in the art. Typically, blacklight sources (which emit long UV light) have been used to reveal fluorescent pigment in paints. Marquees, and various static structures, painted with fluorescent pigment and illuminated with blacklight, were prevalent in the 1920s and 1930s. Soviet Pat. SU 1,627,938 issued Feb. 15, 1991, describes a light that produces a photo-luminescent response in relation to the degree of contamination of wood. Cosmetic use of such systems are not revealed in the prior art.

U.S. Pat. Nos. 4,818,491 issued Apr. 4, 1989 to James D. Fariss and 5,196,705 issued Mar. 23, 1993 to Paul T. Ryan each teach sun exposure monitors which utilize light-responsive fluorescent material. Again, these patents are not directed to cosmetic compositions, nor do they disclose the use of self-tanning agents.

None of the above inventions and patents, taken either singly or in combination, is seen to describe the instant invention as claimed.

SUMMARY OF THE INVENTION

The present invention provides compositions, methods, and kits for cosmetically producing a tanned appearance in desired areas of skin. The composition includes a self-tanning agent together with intimately admixed fluorescent materials in a cosmetic carrier. Without prolonged exposure to intense solar or artificial radiation, applying the self-tanning agent imparts a tanned appearance which develops several hours to a day after application. The fluorescent materials absorb at least one frequency, and emit at another visible frequency. The admixture of self-tanning agent and fluorescent materials allows application of the self-tanning agent selectively only to desired areas of the skin. A light source which emits at the absorbing frequency of the fluorescent materials may be provided together with the compositions in kit form. By illuminating the skin after the composition has been applied and before the self-tanning agent develops its color, any coverage of undesired areas may be easily removed, and any missed desired areas; may be targeted for reapplication.

Accordingly, it is a principal objective of the invention to provide a composition which includes a self-tanning agent together with intimately admixed fluorescent materials that clearly indicate the extent and uniformity of coverage when the composition is applied to skin.

It is another objective of the invention to provide a method for imparting a tanned appearance to skin without prolonged exposure to intense solar or artificial radiation.

It is a further objective of the invention to provide a method which imparts a tanned appearance which is selectively uniform only to desired areas of the skin.

Still another objective of the invention is to provide a kit with which the present method may be practiced.

It is an objective of the invention to provide compositions, methods, and kits for the purposes described which are inexpensive, dependable and fully effective in accomplishing their intended purposes.

These and other objects of the present invention will become readily apparent upon further review of the following description.

DETAILED DESCRIPTION OF THE PREFERRED EMBODIMENTS

The composition of the present invention includes 1) a self-tanning agent, 2) a fluorescent agent, and 3) a cosmetically acceptable carrier.

Many compounds and formulations are known which satisfy the present invention's requirement for a self-tanning agent. These include the α-hydroxy substituted ketones, as described in U.S. Pat. No. 5,302,378, to Crotty et al., previously incorporated, and herein referred to. The self-tanning agent is preferably one or more of: dihydroxyacetone, glucose, xylose, fructose, reose, ribose, pentose, arabinose, allose, tallose, altrose, mannose galactose, lactose, sucrose, erythrose, glyceraldehyde, or 5,6-dihydroxy indole. Most preferably, the self-tanning agent includes at least dihydroxyacetone. Combinations of dihydroxyacetone with polyols or fatty acids are also most preferable.

Fluorescent agents useful in the present invention may be any compound or complex which absorbs light in the infrared, visible, or ultraviolet ranges of the EM spectrum, and emit at a different, visible wavelength. Accordingly, the absorption peak for the fluorescent agent may be for light of wavelengths ($\lambda$) from about $6.00 \times 10^{-10}$ m to about $8.0 \times 10^{-4}$ m. Preferably, the absorption peak is matched with readily available light sources, including blacklight, fluorescent, and incandescent bulbs which correspond to light of wavelengths ($\lambda$) $3 \times 10^{-7}$ m to about $7.8 \times 10^{-7}$ m. The fluorescent agent may emit at any $\lambda$ from $3.90 \times 10^{-7}$ m to about $7.8 \times 10^{-7}$, the visible spectrum. Preferably, the fluorescent agent is chosen to have a fairly narrow or defined absorption and excitation wavelength in the near ultraviolet region, which may be advantageously triggered by available UV light sources, such as a small mercury vapor lamp.

Dyes and pigments which are colorless, or have a neutral, earth or skin tone color under normal lighting conditions, but emit a clearly visible contrasting color to the skin upon specific excitation, are most advantageous in compositions of the present invention. As examples, fluorescent dyes of the rhodamine, fluorescein, napthalimide, or xanthene series may used in the present invention.

These dyestuffs and/or pigments are themselves well known, and are described in the *Encyclopedia of Chemical Technology*, Third Edition, Vol. 14, pp. 527–569 (1981), John Wiley and Sons, Inc. Dyes and pigments which have a relatively short-lived fluorescence, normally unacceptable in conventional applications, may also be advantageously used in the present invention. Accordingly, self-quenching fluorescent agents which maintain fluorescence for at least a few hours upon application may be used.

The fluorescent agent is preferably one or more of: acridine, acridine picrate, acridone, ajacine, ambergris, anthracene-1-carboxylic acid, anthracene-2-carboxylic acid, anthracene dicarboxylic acid, auramine, benzyl acetate, borneol, calcium hydroxyquinolinate, ergometrine, erythrosine, ethyl β-naphtholate, iron hydroxyquinolinate, fluorescein, ionone, musk ambrette, musk ketone, musk xylol, myosalvarsan, pentachloroethane, phaetophytin, phycoerythrin, podophyllin, protoporphyrin, pyocyanine, quinine, rhodamine, rose bengal, uranine, uric acid, veronal, zinc hydroxyquinoline sulfonate,, zinc resinate, or zinc urobilinate.

Most preferably, the fluorescent agent is chosen to be nontoxic and well accepted by the skin. However, fluorescent agents not normally well tolerated on the skin may still be used in microencapsulated form, whereby the agent is shielded from the actual contact with the skin, through optically transmissive polymer coatings. Microencapsulation methods are well known in the art, and form no part of the present invention. The disclosure of Bradner, U.S. Pat. No. 3,988,437, discussed supra, is herein incorporated by reference. See in particular the discussion of microencapsulation in col. 6, lines 14–39.

The carrier may include various cosmetic bases and may take the form of a liquid, cream lotions, ointments, powders, or the like. Perfumes, vitamins, skin feel agents, and skin penetration enhancers may be optionally included in the base. The cosmetic base or carrier is preferably optically transmissive to both the excitation and emission wavelengths of the fluorescent agent. However, translucent or opaque bases may also be used, so long as sufficient amounts of the fluorescent agent are available on the exposed surface, once the cosmetic base is applied. The Bradner patent, as well as the Andreadis et al. patent are again referred to as representative carrier formulations which may used in the present invention.

To formulate the compositions of the present invention, the self-tanning agent, the carrier's efficacy in delivering the self-tanning agent to the skin, as well as any skin penetration enhancement should be considered. Accordingly, liquids, lotions, and ointments which may be substantially worked into the skin may require less of the self-tanning agent, and are therefore preferred over dry formulations such as powders. The fluorescent agent is provided in amounts sufficient to provide detectable emissions upon excitation.

The amount of fluorescent agent present is most dependent upon the agent selected and the quantity of excitation provided thereto. These amounts are readily determined from the known characteristics of the selected fluorescent agent. For highly biocompatible agents, the concentration of fluorescent materials may be advantageously selected to provide emission at the lowest amount of excitation. Conversely, the concentration of fluorescent agent may be decreased when a higher intensity of excitation is utilized at frequencies, of the near UV range, considered safe in the art.

For example, in liquid, lotion, or cream formulations, where an α-hydroxy ketone is used as the self-tanning agent, and the fluorescent agent is of the rhodamine, fluorescein, napthalimide, or xanthene series of dyes, a concentration of about 0.05–90% by weight α-hydroxy ketone, 0.01–10% by weight dye, and the remainder carrier may be used. Preferably, the composition includes 0.4–25% α-hydroxy ketone and 0.5–1% dye, and the remainder carrier. Most preferably, dihydroxyacetone is included as the α-hydroxy ketone of choice.

The method of the present invention imparts an evenly distributed tanned appearance to desired areas of skin with the following steps.

a) A composition which includes the self-tanning agent, the fluorescent agent, and the cosmetic carrier is applied to desired areas of the skin.

b) The skin is exposed to a light source of frequency and intensity to produce fluorescence in the composition through visible emission by the fluorescent agent.

c) The skin surface is examined to determine whether the desired areas of coverage are producing fluorescence, and whether areas of the body surface, such as nails or palms which are to be excluded from the self-tanning agent are not.

d) Where desired areas of the skin show no fluorescence, the composition is reapplied.

e) Where undesired areas of the skin show fluorescence, the composition is removed.

f) The self-tanning agent is then allowed to develop the color, thereby imparting a tanned appearance to desired areas exclusively.

This method allows users of self-tanning products to confidently predict and control the extent of coverage of the resultant tan. The substantial removal of uncertainty is seen as a decided advantage over the prior art, where coverage may only be accessed when correction is no longer possible.

The present invention is most practically carried out with a kit for performing the above process. This may advantageously provide a vessel containing the artificial tanning composition, and a light source capable of producing fluorescence in the composition. The kit may be provided as a way to package the necessary elements of the invention conveniently together for distribution, or may be an end user storage medium, such as a compartmentalized case. The individual elements may then be optimized to work together. For example, a small mercury vapor lamp, and a composition which includes a rhodamine, fluorescein, napthalimide, or xanthene series of dyes which are optimally excited by the lamp may be provided in kit form.

It is to be understood that the present invention is not limited to the embodiments described above, but encompasses any and all embodiments within the scope of the following claims.

I claim:

1. A method for imparting a tanned appearance simulative a tan derived from solar radiant exposure by effecting color change in selected areas of skin of a human body surface comprising the steps:

a) selecting areas of skin for color change;

b) applying an artificial tanning composition comprising a self-tanning agent, a fluorescent agent, and a cosmetically acceptable carrier to approximately the selected areas of skin, said self-tanning agent is selected from the group consisting of dihydroxyacetone, glucose, xylose, fructose, reose, ribose, pentose, arabinose, allose, tallose, altrose, mannose galactose, lactose, sucrose, erythrose, gtyceraldehyde, and 5,6-dihydroxy indole; and said fluorescent agent includes a fluorescent dye selected from the group consisting of rhodamine, fluorescein, napthalimide, and xanthene dye;

c) exposing the body surface to a light source of frequency and intensity to produce fluorescence in said composition;

d) inspecting the body surface to determine whether said fluorescence produced is limited to substantially said selected areas of skin;

e) reapplying said composition to said selected areas of skin which show no fluorescence;

f) removing said composition from areas of the body surface outside those selected areas of skin which show fluorescence; and g) allowing sufficient time for said self-tanning agent of said composition to impart a tanned appearance to substantially said selected areas of skin.

2. The method according to claim 1, wherein said self-tanning agent includes dihydroxyacetone.

3. A kit for performing the method of claim 1 comprising:

said artificial tanning composition, and a light source capable of producing visible fluorescence in said composition.

4. The method. according to claim 1, wherein said artificial tanning composition consists essentially of from about 0.05 to about 90 percent by weight of said self-tanning agent; from about 0.01 to about 10 percent by weight of a fluorescent agent selected from the group of fluorescent dyes consisting of rhodamine, fluorescein, napthalimide, and xanthene dyes; and the remainder said cosmetically acceptable carrier.

5. The method according to claim 4, wherein said artificial tanning composition consists essentially of from about 0.4 to about 25 percent by weight of said self-tanning agent; from about 0.5 to about 1 percent by weight of said fluorescent dye; and the remainder said cosmetically acceptable carrier.

6. The method according to claim 5, wherein said self-tanning agent is dihydroxyacetone.

7. The method according to claim 6, wherein said fluorescent dye is fluorescein.

8. The kit according to claim 3, wherein said artificial tanning composition. consists essentially of from about 0.5 to about 90 percent by weight of said self-tanning agent; from about 0.01 to about 10 percent by weight of said fluorescent agent; and the remainder said cosmetically acceptable carrier; and said light source emits a long wavelength fluorescent light in the near UV region.

9. The kit according to claim 8, wherein said artificial tanning composition consists essentially of from about 0.4 to about 25 percent by weight of said self-tanning agent; from about 0.5 to about 1 percent by weight of said fluorescent dye; and the remainder said cosmetically acceptable carrier.

10. The kit according to claim 9, wherein said self-tanning agent is dihydroxyacetone.

11. The kit according to claim 10, wherein said fluorescent dye is fluorescein.

* * * * *